(12) United States Patent
List et al.

(10) Patent No.: US 8,920,341 B2
(45) Date of Patent: Dec. 30, 2014

(54) TEST STRIP DEVICE AND METHOD FOR ANALYZING A BODY FLUID

(75) Inventors: Hans List, Hesseneck-Kailbach (DE);
Wilhelm Leichner, Mannheim (DE);
Volker Zimmer, Morbach (DE);
Matthias Greuter, Stäfa (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 554 days.

(21) Appl. No.: 12/757,069

(22) Filed: Apr. 9, 2010

(65) Prior Publication Data

US 2010/0286561 A1    Nov. 11, 2010
US 2011/0282244 A9    Nov. 17, 2011

Related U.S. Application Data

(63) Continuation of application No. PCT/EP2008/063503, filed on Oct. 9, 2008.

(30) Foreign Application Priority Data

Oct. 12, 2007    (EP) .................................... 07118411

(51) Int. Cl.
*A61B 5/00*    (2006.01)
*A61B 5/151*    (2006.01)
*A61B 5/15*    (2006.01)

(52) U.S. Cl.
CPC ........... *A61B 5/1411* (2013.01); *A61B 5/15146* (2013.01)
USPC ........................................... 600/583; 436/44

(58) Field of Classification Search
USPC .......................................... 600/583; 436/44
See application file for complete search history.

(56) References Cited

U.S. PATENT DOCUMENTS

| 4,218,421 | A | 8/1980 | Mack, Jr. et al. |
| 4,924,879 | A | 5/1990 | O'Brien |

(Continued)

FOREIGN PATENT DOCUMENTS

| DE | 28 03 345 B1 | 6/1979 |
| DE | 198 19 407 A1 | 11/1999 |

(Continued)

OTHER PUBLICATIONS

DE 198 19 407 A1 Machine Translation, Nov. 11, 1999.

(Continued)

*Primary Examiner* — Max Hindenburg
*Assistant Examiner* — Renee Danega
(74) *Attorney, Agent, or Firm* — Roche Diagnostics Operations, Inc.

(57) ABSTRACT

The invention concerns a test tape device for analyzing a body fluid having a carrier tape, a plurality of lancing elements arranged on the carrier tape which are provided with a tip that can puncture a body part and a collecting structure that takes up the body fluid obtained during the puncture, and test fields mounted on the carrier tape each being associated with a lancing element and can have body fluid applied thereto. According to the invention it is proposed that the lancing elements are each movably attached to the carrier tape by a coupling member and that a used lancing element can be brought into contact with a test field by a transfer movement from a usage position distant from a test field into a contact position so that body fluid can be transferred from the collecting structure onto the test field.

19 Claims, 3 Drawing Sheets

(56) References Cited

U.S. PATENT DOCUMENTS

| | | | |
|---|---|---|---|
| 5,077,010 A | 12/1991 | Ishizaka et al. | |
| 7,955,271 B2 * | 6/2011 | Roe et al. | 600/583 |
| 2003/0199906 A1 * | 10/2003 | Boecker et al. | 606/181 |
| 2003/0211619 A1 | 11/2003 | Olson et al. | |
| 2005/0201897 A1 | 9/2005 | Zimmer et al. | |
| 2005/0245845 A1 | 11/2005 | Roe et al. | |
| 2005/0245954 A1 | 11/2005 | Roe et al. | |
| 2006/0247555 A1 | 11/2006 | Harttig | |
| 2006/0293611 A1 | 12/2006 | Calasso et al. | |
| 2007/0016103 A1 | 1/2007 | Calasso et al. | |
| 2007/0038149 A1 | 2/2007 | Calasso et al. | |
| 2007/0038150 A1 | 2/2007 | Calasso et al. | |
| 2007/0173740 A1 | 7/2007 | Chan et al. | |
| 2008/0103415 A1 | 5/2008 | Roe et al. | |
| 2008/0269791 A1 | 10/2008 | Hoenes et al. | |

FOREIGN PATENT DOCUMENTS

| | | |
|---|---|---|
| EP | 1 360 935 A1 | 11/2003 |
| EP | 1 424 040 A1 | 6/2004 |
| EP | 1 790 288 A1 | 5/2007 |
| EP | 1 967 139 A1 | 9/2008 |
| WO | WO 2004/047642 A1 | 6/2004 |
| WO | WO 2005/104948 A1 | 11/2005 |
| WO | WO 2005/107596 A2 | 11/2005 |
| WO | WO 2007/147494 A2 | 12/2007 |

OTHER PUBLICATIONS

DE 28 03 345 B1 English Language Translation, Jan. 26, 1978.
International Patent Application PCT/EP2008/063503 International Search Report mailed Jan. 12, 2009.

* cited by examiner

TEST STRIP DEVICE AND METHOD FOR ANALYZING A BODY FLUID

CROSS-REFERENCE TO RELATED APPLICATION

This application is a continuation of International Patent Application No. PCT/EP2008/063503, filed Oct. 9, 2008, which claims the benefit of European Patent Application No. 07118411.3, filed Oct. 12, 2007, the entire disclosures of which are hereby incorporated by reference.

BACKGROUND

The invention concerns a test tape device for analyzing a body fluid especially for blood sugar tests having a carrier tape that can be wound onto or is wound onto a spool, a plurality of lancing elements arranged on the carrier tape which are provided with a tip that can puncture a body part and a collecting structure that takes up the body fluid obtained during the puncture, and test fields mounted on the carrier tape each being associated with a respective lancing element and can have body fluid applied thereto. The invention additionally concerns a corresponding method for analyzing a body fluid.

A test tape device of this type is known from WO2005/107596. A multilayer test tape is described therein in which a strip of tape carrying lancets is joined in a sandwich-like manner with a strip of tape provided with test fields. The test fields are in a fixed position in relation to a capillary groove of the lancets which delivers the body fluid by means of capillary transport. The tangential orientation of the lancets facing forwards in relation to the tape running direction is retained even during a tape deflection so that the lancet tips travel in a relatively large circular path until they have completely executed the change in direction of the tape. The sandwich arrangement also makes the overall structure relatively large. In addition embodiments are described in which the test fields are arranged alternately with the lancets and are spaced apart longitudinally on the tape in order that the user can actively apply a drop of blood after the puncture.

SUMMARY

Starting from this, the object of the invention is to further improve the products and methods known in the prior art and to design them such that a simplified handling without complicated actuating elements is possible in a compact arrangement.

The combination of features stated in the independent patent claims is proposed to achieve this object. Advantageous embodiments and further developments of the invention are derived from the dependent claims.

The invention is based on the idea of avoiding a long flow transport of the sample from the collecting structure onto the test field and instead to actively move the lancing element into a fluidic contact position. Accordingly it is proposed according to the invention that the lancing elements are each attached with limited movement capability to the carrier tape by a coupling member and that a used lancing element can be brought into contact or fluidic connection with a test field by a transfer movement from a usage position distant from a test field into a contact position that is executed by the lancing element itself so that body fluid is transferred directly from the collecting structure onto the test field. In this manner the lancing element can be kept very small and reduced to a lancing tip with a collecting volume. The time of sample transfer can be exactly determined by apparative measures. Additional handling by the user is not necessary for the sample transfer. At the same time the firm connection with the tape via the coupling member ensures that the lancing elements are stored in a correct position and can be simply disposed of. Moreover, sterilization is considerably simplified by the distance between the lancing element and sensitive detection chemistry on the test field in the initial state.

The orientation of the lancing elements relative to the tape can advantageously be reversed by the transfer movement where the lancing elements can be oriented in the longitudinal direction of the carrier tape at least in the contact position and can be contacted with an associated test field by a pivoting movement and in particular a folding movement. However, it is also conceivable that the tips of the lancing elements point at right angles to the longitudinal tape direction.

Another advantageous embodiment provides that the lancing elements remain permanently connected to the tape by means of the coupling member during the transfer movement so that a complicated detachment is not required.

The lancing elements are particularly preferably hinged on the carrier tape in a proximal region spaced apart from the tip by means of a joint or hinge as a coupling member. This can be achieved in a simple manner by the lancing elements being pivotally connected to the carrier tape by means of a bending joint and in particular a film joint. A further improvement is achieved by means of the fact that the lancing elements are covered in a preferably sterile manner on the carrier tape by a foil or foil bag where the foil or foil bag is permanently connected to the carrier tape and to a proximal section of the respective lancing element.

The test fields advantageously have a reagent layer which is designed to detect an analyte in the body fluid.

Another particularly advantageous embodiment provides that the transfer movement of a lancing element can be triggered by advancing the carrier tape so that a complicated transfer mechanism is not necessary. This can be achieved in a simple manner in that the carrier tape is guided laterally past a retaining member and that the retaining member forms a stop obstacle for a lancing element which starts up during the tape transport preferably for folding down the lancing element. In this connection it is also preferable that the retaining member is located in the area of a deflection point for the carrier tape and the tip of the lancing elements can be lifted from the carrier tape at the deflection point.

In order to enable a defined lancing movement in connection with the tape that is also being moved, it is advantageous when the lancing elements are held in a gripping manner at a deflection point for the carrier tape by a holder or fastener in order to execute a lancing movement. Another improvement can be achieved in that the deflection point is arranged on a carriage that is also moved during the lancing movement.

In order to reliably ensure the liquid transfer, it is advantageous when the carrier tape is guided past a holding-down device which is formed in particular by a leaf spring, wherein the holding-down device presses a lancing element which passes through against a test field.

If a large number of self-tests have to be carried out on a regular basis, it is advantageous for the user when the carrier tape can be replaced as a single-use article preferably in the form of a tape cassette. Hence, the invention also concerns a test tape as a disposable for use in a test tape device according to the invention.

In order to solve the above-mentioned object, it is proposed with regard to the process that the lancing elements are each held in a movable manner on the carrier tape by a coupling member and that the lancing elements are brought into contact with a test field by a transfer movement from a usage position distant from a test field into a contact position so that body fluid is transferred from the collecting structure onto the test field.

BRIEF DESCRIPTION OF THE DRAWINGS

The invention is further elucidated in the following on the basis of the embodiment examples shown schematically in the drawing.

DETAILED DESCRIPTION

Figure 1:
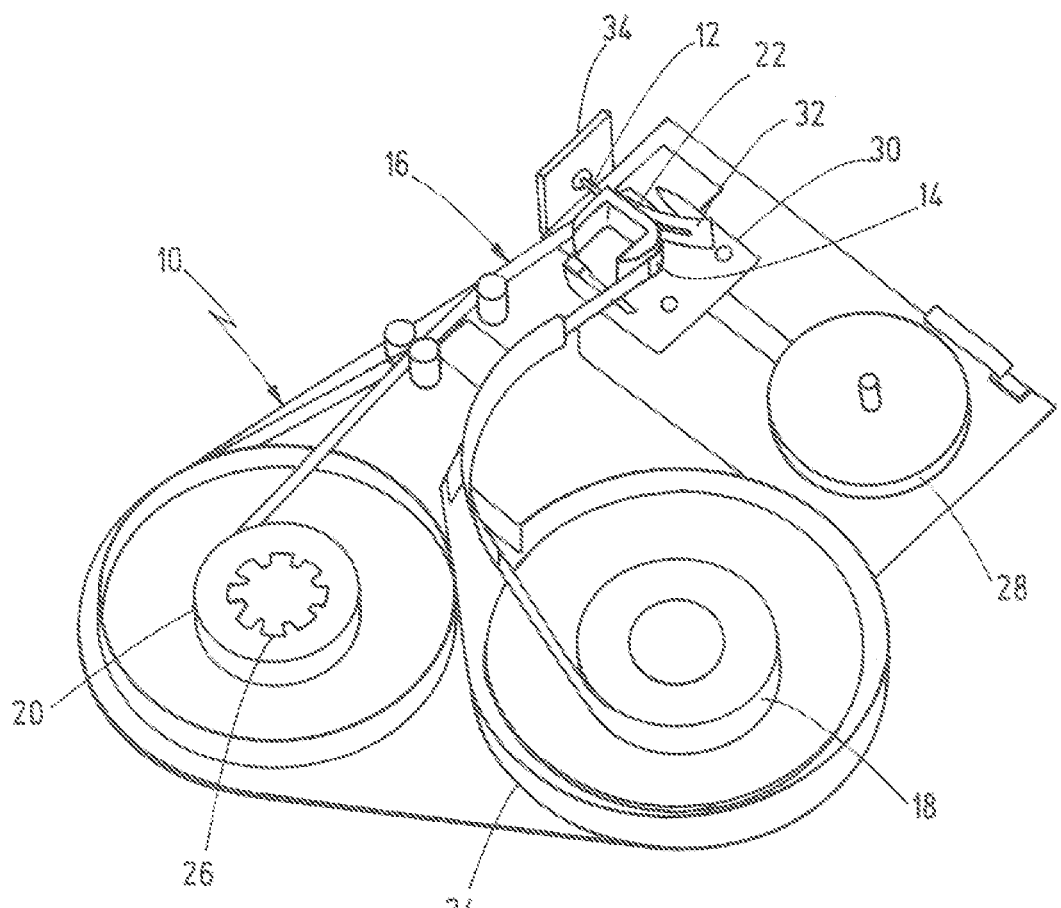
FIG. 1 shows a test tape device in a diagrammatic view.

The test tape device 10 shown in the drawing enables a plurality of disposable lancing elements 12 and test elements 14 to be provided in the form of a test tape 16 for blood glucose determinations or other analyses on samples of body fluids in which the body fluid is transferred onto a test field by a movement of a lancing element relative to the test tape.

As shown in FIG. 1 the unused test tape 16 can be wound off a supply spool 18, whereas used tape material can be disposed of on a take-up spool 20. It is also conceivable that at least the supply spool is replaced by a chamber containing folded tape. The section of test tape that is in use is guided over a deflection point 22 and in this process is exposed for measuring purposes. The spools 18, 20 are preferably provided as consumables in the form of a tape cassette 24. In this manner a tape magazine is provided which allows a plurality of tests before the consumable has to be replaced.

In order to simplify blood glucose measurements as self-tests for a user, the device 10 is designed for a substantially automatic measuring process by means of a compact hand-held device that is only shown diagrammatically. For this purpose a lancing drive 28 is also provided in addition to a tape drive 26 which engages with the take-up spool 20. The lancing drive 28 is connected with a carriage 30 for a linear movement and said carriage 30 carries the deflection point 22 and a gripper 32 for the lancing element 12. Thus, a lancing element 12 brought into an active position can pierce the skin of a finger or body part that is placed on a finger rest 34 through an opening in order to remove a small volume of blood for analytical purposes.

Figure 2:
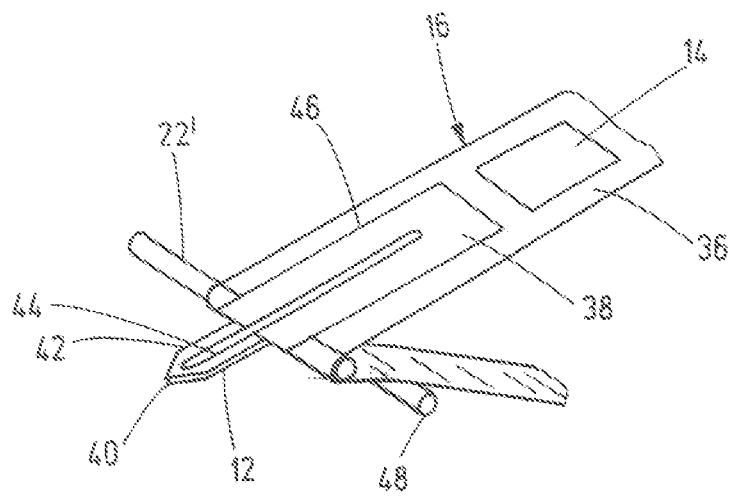
FIG. 2 shows a section of test tape with a lancing element that can be folded onto a test field in a perspective view.

According to FIG. 2 the test tape 16 has a flexible carrier tape 36 on which the lancing elements 12 are each pivotally mounted via a coupling member 38 so that after sample uptake they can be brought into a contact position in fluidic connection with an associated test field 14 by means of a transfer movement from the shown usage position.

The lancing elements 12 stored on the carrier tape 36 have a sharp tip 40 at their distal end for puncturing the skin. The elongate shaft 42 which adjoins the tip is provided with a groove-shaped or slot-shaped capillary channel 44 for collecting the body fluid i.e. blood and/or tissue fluid that is obtained by the skin puncture.

In its initial position the lancing shaft 42 is aligned in the running direction of the carrier tape. In this alignment each of the lancing elements 12 is attached by a foil bag 46 formed by a glued-on strip of foil which ensures that they are covered in a sterile manner and at the same time forms the coupling element in the proximal area of the lancing element. For this purpose the rear area of the foil bag 46 is permanently joined to the shaft 42 and to the carrier tape 36. The flexible foil bag 46 thus acts as a film joint that can be bent around a bending line in a transverse tape direction in order to allow the lancing element 12 to be folded against the test field 14.

The folding down of the lancing element 12 serves as a transfer movement in order to enable a transfer of liquid onto a downstream test field 14 on the carrier tape 36 which is located in the pivoting area. The control of this movement solely on the basis of the tape advance can be simply understood on the basis of FIG. 2. Firstly the carrier tape 36 is deflected at such an acute angle on the deflection roller 22' that the tip 40 of a lancing element 12 running over the deflection roller pierces the foil bag 46 and is exposed for a skin puncture. During subsequent transport the exposed distal section of the lancing element 12 runs up against a retaining pin 48 which folds it around the coupling member 38 of the foil bag 46. In the folded down contact position the tip 40 points against the running direction of the tape while the capillary channel 44 is in fluidic contact with the test field 14 in order to transfer body fluid.

In order to detect an analyte in the body fluid, such as blood glucose, the test fields 14 are provided with a suitable reagent layer which reacts with a colour change during liquid uptake. This change in colour can be detected by a suitable optical detector that is not shown and displayed after measurement processing as a measurement result for the user.

Figure 3:
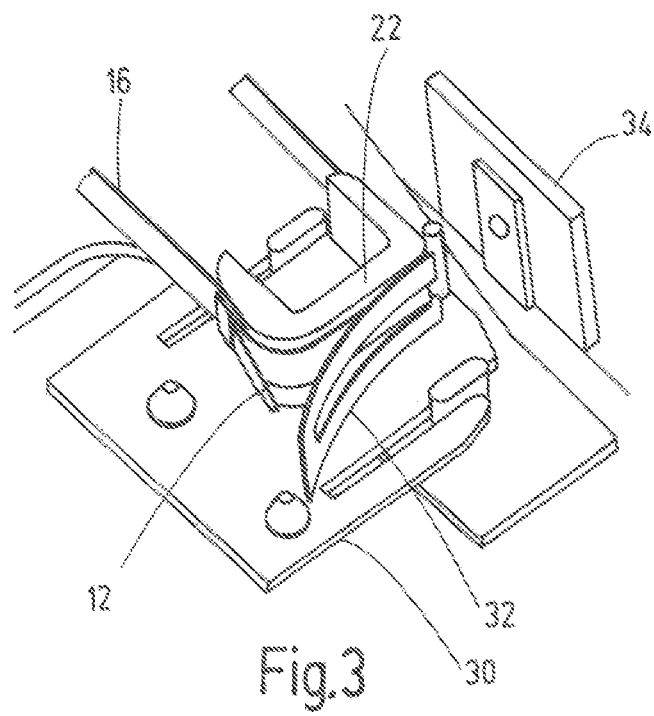
FIGS. 3 to 6 show various functional positions of a lancing element on the test tape in a sectional enlargement of FIG. 1.
Figure 4:
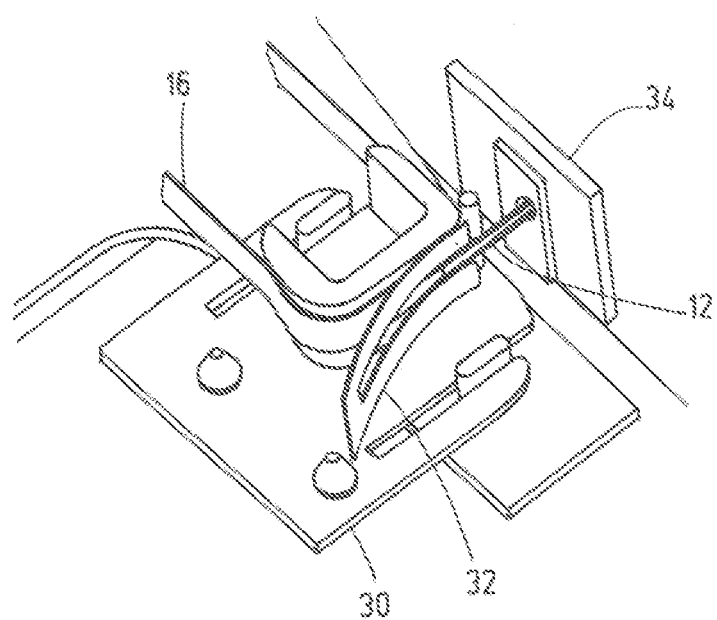
Figure 5:
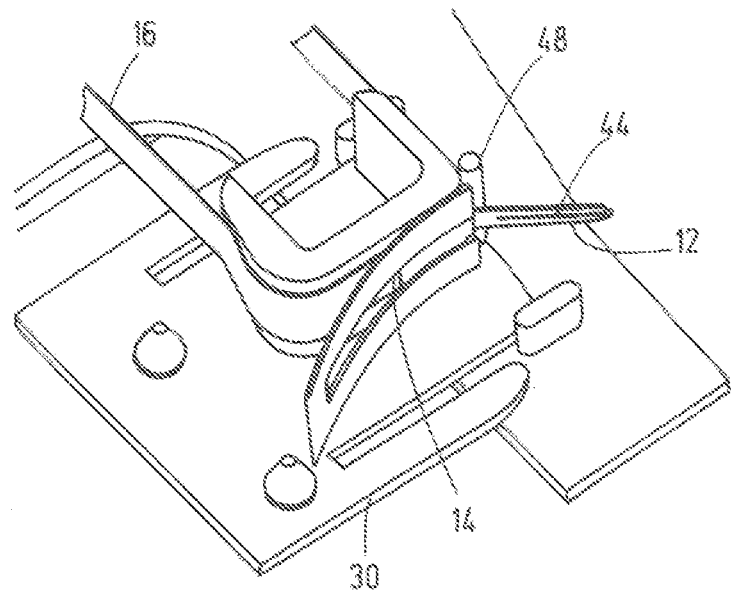
Figure 6:
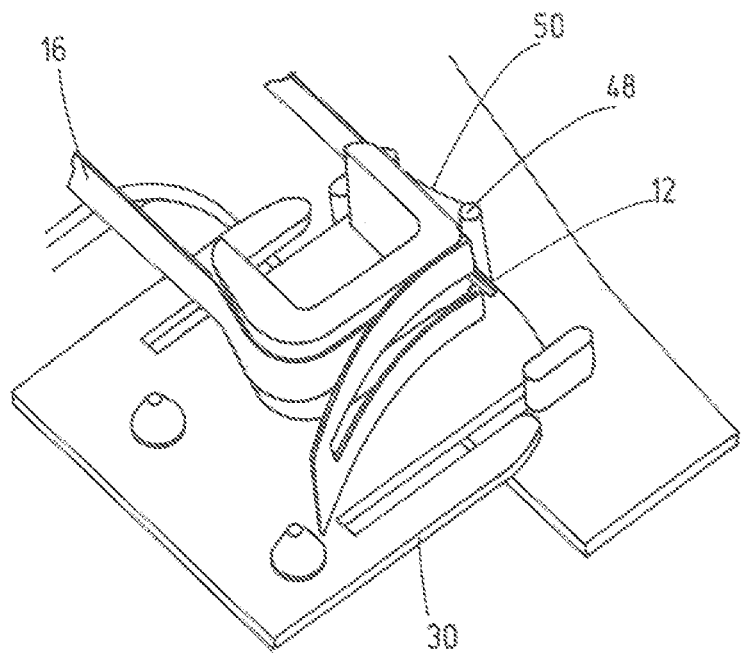

The basic sequence of the process is shown in FIGS. 3 to 6 for the embodiment example according to FIG. 1 in some functional positions. FIG. 3 shows a situation corresponding to FIG. 2 in which the lancing element 12 is exposed by the deflection of the tape at the deflecting point 22. After a suitable tape advance the lancing element 12 is held in a gripping manner by the gripper 32 in order to execute a lancing movement through the finger rest 34 while the carriage 30 is pushed forwards (FIG. 4). In this process the deflected section of tape is moved together with the lancing element 12 in the puncture direction. Thus, the lancing element 12 can remain permanently connected to the carrier tape via the coupling member 38. Subsequently the folding movement of the lancing element 12 can be triggered by further tape transport according to FIG. 5 during which the retaining pin 48 located at the side of the tape acts as a stop obstacle. Finally according to FIG. 6 the contact position is reached in which the collected body fluid is transferred from the lancing element 12 onto the associated test field 14. This contact can be further intensified by a holding-down device that presses against the tape as it runs through which is for example in the form of a leaf spring 50.

Thus, neither a separate drive unit nor user handling is required for the targeted transfer of liquid. It is basically also possible to take up the body fluid by means of collecting elements which are not designed for a puncture but have a holding volume for liquid uptake.

The invention claimed is:

1. A test tape device for analyzing a body fluid for blood sugar tests having a carrier tape that can be wound onto or is wound onto a spool, a plurality of lancing elements arranged on the carrier tape which are provided with a tip that can puncture a body part and a collecting structure that takes up the body fluid obtained by the puncture, and test fields mounted on the carrier tape each being associated with a lancing element and can have body fluid applied thereto, characterized in that the lancing elements are each movably attached to the carrier tape by a coupling member, and that a used lancing element can be brought into fluidic connection with a test field by a transfer movement executed by the lancing element from a usage position distant from a test field into a contact position, so that body fluid is transferred directly from the collecting structure onto the test field, wherein each lancing element is covered in a sterile manner by a cover foil connected to the carrier tape to form a foil bag around each lancing element, wherein the lancing element is configured to puncture the cover foil, characterized in that the test fields have a reagent layer which is designed to detect an analyte in the body fluid.

2. The test tape device according to claim 1, characterized in that the orientation of the lancing elements relative to the carrier tape can be reversed by the transfer movement.

3. The test tape device according to claim 1, characterized in that the elongate lancing elements can be oriented in the longitudinal direction of the carrier tape at least in the contact position.

4. The test tape device according to claim 1, characterized in that the lancing elements can be contacted with an associated test field by a pivoting movement and in particular a folding movement.

5. The test tape device according to claim 1, characterized in that the lancing elements remain permanently connected to the tape by means of the coupling member during the transfer movement.

6. The test tape device according to claim 1, characterized in that the lancing elements are hinged on the carrier tape in a proximal region that is spaced apart from the tip by means of a joint or hinge as a coupling member.

7. The test tape device according to claim 1, characterized in that the lancing elements are pivotally connected to the carrier tape by means of a bending joint and in particular a film joint.

8. The test tape device according to claim 1, characterized in that the transfer movement of a lancing element can be triggered by advancing the carrier tape.

9. The test tape device according to claim 1, characterized in that the carrier tape is guided laterally past a retaining member and that the retaining member forms a stop obstacle for a lancing element which starts up during the tape transport preferably for folding down the lancing element.

10. The test tape device according to claim 9, characterized in that the retaining member is located in the area of a deflection point for the carrier tape and the tip of the lancing elements can be lifted from the carrier tape at the deflection point.

11. The test tape device according to claim 1, characterized in that the lancing elements are held at a deflection point for the carrier tape by a gripper in order to execute a lancing movement.

12. The test tape device according to claim 11, characterized in that the deflection point is arranged on a carriage that is also moved during the lancing movement.

13. The test tape device according to claim 1, characterized in that the carrier tape is guided past a holding-down device which is formed in particular by a leaf spring, wherein the holding-down device presses a lancing element which passes through against a test field.

14. The test tape device according to claim 1, characterized in that the carrier tape can be replaced as a single-use article preferably in the form of a tape cassette.

15. The test tape for insertion into a test tape device according to claim 1 preferably in the form of a replaceable tape cassette.

16. A method for analyzing a body fluid for blood sugar tests, comprising:
providing a plurality of lancing elements and associated test fields on a windable carrier tape, wherein the lancing elements are provided with a collecting structure, wherein the lancing element is covered by a foil holding each of the lancing elements in a movable manner on the carrier tape by means of a coupling member;
exposing the lancing element by piercing the foil with a tip of the lancing element, wherein said exposing includes deflecting the carrier tape at an acute angle on a deflection roller;
taking up the body fluid with the collecting structure of the lacing elements;
bringing one of the lancing elements into contact with one of the test fields by a transfer movement from a usage position that is distant from the test field into a contact position so that the body fluid is transferred directly from the collecting structure onto the test field; and
detecting an analyte in the body fluid with the test field.

17. The method of claim 16, further comprising:
wherein the collecting structure includes a capillary channel;
wherein the transfer movement includes folding down the lancing element to transfer the body fluid from the capillary channel onto the test field;
wherein the orientation of the lancing element relative to the carrier tape is reversed by the transfer movement; and
controlling the transfer movement by advancing the carrier tape.

18. The method of claim 17, further comprising:
pressing the lancing element against the carrier tape with a holding down device to intensify contact between the lancing element and the test field when at the contact position.

19. A test tape device for analyzing a body fluid for blood sugar tests having a carrier tape that can be wound onto or is wound onto a spool, a plurality of lancing elements arranged on the carrier tape which are provided with a tip that can puncture a body part and a collecting structure that takes up the body fluid obtained by the puncture, and test fields mounted on the carrier tape each being associated with a lancing element and can have body fluid applied thereto, characterized in that the lancing elements are each movably attached to the carrier tape by a coupling member, and that a used lancing element can be brought into fluidic connection with a test field by a transfer movement executed by the lancing element from a usage position distant from a test field into a contact position, so that body fluid is transferred directly from the collecting structure onto the test field, wherein each lancing element is covered in a sterile manner by a cover foil connected to the carrier tape to form a foil bag around each lancing element, wherein the lancing element is configured to puncture the cover foil, wherein a rear area of the foil bag is joined to a shaft of the lancing element and the carrier tape to form the coupling member, wherein the foil bag acts as a film joint to allow the lancing element to be folded against the test field.

* * * * *

UNITED STATES PATENT AND TRADEMARK OFFICE
CERTIFICATE OF CORRECTION

PATENT NO. : 8,920,341 B2  
APPLICATION NO. : 12/757069  
DATED : December 30, 2014  
INVENTOR(S) : Hans List et al.

Page 1 of 1

It is certified that error appears in the above-identified patent and that said Letters Patent is hereby corrected as shown below:

In the Claims  
Col. 6, Claim 16, line 14, replace "lacing elements;" with --lancing elements;--

Signed and Sealed this  
Fifth Day of May, 2015

Michelle K. Lee  
*Director of the United States Patent and Trademark Office*